United States Patent [19]

Nagai et al.

[11] 4,390,520

[45] Jun. 28, 1983

[54] ANTIPHLOGISTIC ANALGESIC ADHESIVE

[75] Inventors: Hidetaka Nagai, Hachioji; Yasushi Wada, Tachikawa; Ichiro Kobayashi, Osaka; Mitsuru Tamada, Osaka; Keiichi Ushiyama, Osaka; Toshiyuki Yamamoto, Osaka, all of Japan

[73] Assignees: Nitto Electric Industrial Co., Ltd., Osaki; Kawa Co., Ltd., Aichi, both of Japan

[21] Appl. No.: 248,912

[22] Filed: Mar. 30, 1981

[30] Foreign Application Priority Data

Oct. 30, 1980 [JP] Japan .................................. 55-153407

[51] Int. Cl.³ ........................ A61F 13/00; A61K 9/70; A61L 15/00
[52] U.S. Cl. ....................................... 424/28; 424/274
[58] Field of Search ........................................... 424/28

[56] References Cited

U.S. PATENT DOCUMENTS 3,632,740 1/1972 Robinson et al. ...................... 424/28
3,731,683 5/1973 Zaffaroni ............................... 424/28

Primary Examiner—Stanley J. Friedman
Attorney, Agent, or Firm—Sughrue, Mion, Zinn, Macpeak & Seas

[57] ABSTRACT

An antiphlogistic analgesic adhesive which comprises
  a flexible substrate and
  an indomethacin containing pressure-sensitive adhesive layer closely contacting said flexible substrate, wherein said pressure-sensitive adhesive layer comprises a mixture of
    (a) indomethacin,
    (b) a copolymer of (i) an alkyl acrylate having 4 to 11 carbon atoms in the alkyl moiety and (ii) a functional monomer having a functional group in the molecule thereof and/or a vinyl monomer, which has pressure-sensitive adhesive properties at room temperature, and
    (c) an absorption accelerating assistant which maintains said indomethacin in a solubilized state in said copolymer and has skin diffusibility.

13 Claims, 1 Drawing Figure

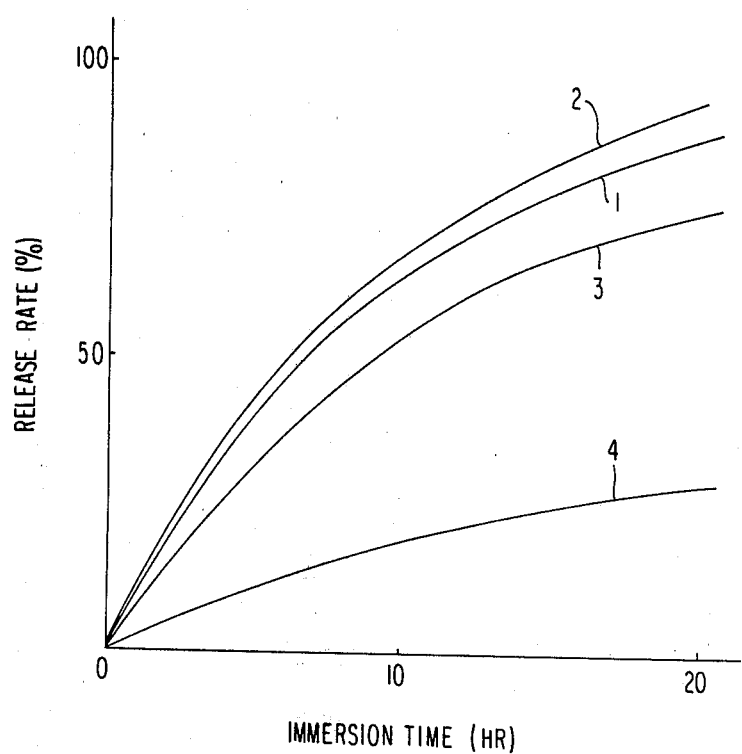

4,390,520

ANTIPHLOGISTIC ANALGESIC ADHESIVE

FIELD OF THE INVENTION

The present invention relates to an antiphlogistic analgesic adhesive using indomethacin as an active ingredient and, in greater detail, to a novel antiphlogistic analgesic adhesive capable of curing the affected part under the skin when applied directly to the skin by sure absorption of the active ingredient through the skin.

BACKGROUND OF THE INVENTION

Indomethacin is known as a non-steroid antiphlogistic having an excellent antiphlogistic effect. Indomethacin is believed to have an antiphlogistic function 85 times that of phenylbutazone (rat granuloma suppressive function), an anodyne function of 75 times that of aspirin (Rat Randall-Selitto's method) and an antipyretic function of 20 times that of phenylbutazone (pyrogen-febrile rabbit). Accordingly, it has been widely used hitherto, for treating symptoms such as chronic rheumatoid arthritis, osteoarthritis, spondylosis deformans or periarthritis humeroscapularis, etc., and moreover inflammation and pain after surgery or an external injury.

Indomethacin is used generally orally or as a suppository.

Although indomethacin has a strong therapeutic effect, it causes side effects such as gastro-intestinal trouble, and, therefore, it is especially restricted for peptic ulcer patients. Recently, in order to reduce such side effects, ointments containing indomethacin has been proposed, which are applied directly to the affected part to cure by localized absorption of the indomethacin through the skin. According to this method, sufficient reduction of side effects can be expected and the above described therapeutic effects of indomethacin can be safely exhibited.

However, even though ointments have the above described advantage, they have the disadvantage that the correct dosage to the body is difficult to control, because the ointment applied to the surface of the body is wiped away by clothes and, further, the release rate of the indomethacin from the ointment is not definite. Further, as a result of wiping away by clothes, clothes are soiled.

Recently, as a means for solving these various disadvantages caused by application of the ointment, a product which is obtained by mixing a drug such as a corticosteroid with a pressure-sensitive adhesive composition and applying the mixture to a substrate to form a coated film has been proposed.

In products containing corticosteroids, the therapeutic effect can be attained only by contacting the steroids with the skin, because of their characteristics on the clinical use.

On the contrary, in case of indomethacin, the desired effect cannot be attained by only forming a pressure-sensitive adhesive layer containing indomethacin to a substrate, because it is necessary for indomethacin to penetrate deeply under the skin in order to obtain the therapeutic effect.

SUMMARY OF THE INVENTION

Accordingly, a first object of the present invention is to provide an antiphlogistic analgesic adhesive containing a large amount of indomethacin in a skin absorptive member, which is capable of releasing the indomethacin to the skin and supply the indomethacin deeply under the skin.

Further, a second object of the invention is to provide an antiphlogistic analgestic adhesive which firmly adheres to the skin for a desired period of time and does not leave residure on the skin when stripped off.

Moreover, a third object of the present invention is to provide an antiphlogistic analgesic adhesive which does not leave undesirable traces on the skin or does not result in a disagreeable sense of tension when applied to the skin.

These and other objects are attained to by this invention which provides an antiphlogistic analgesic adhesive comprising
a flexible substrate and
an indomethacin-containing pressure-sensitive adhesive layer closely contacting the flexible substrate, wherein the pressure-sensitive adhesive layer comprises a mixture of
(a) indomethacin
(b) a copolymer of (i) an alkyl acrylate having 4 to 12 carbon atoms in the alkyl moiety thereof and (ii) a functional monomer having a functional group in the molecule and/or a vinyl monomer, which has pressure-sensitive adhesive properties at room temperature, and
(c) an absorption accelerating assistant which maintains the indomethacin in a solubilized state in the copolymer and which is skin diffusible.

BRIEF DESCRIPTION OF THE DRAWING

The FIGURE shows the relation between the immersion time and release rate for indomethacin in each adhesive obtained in Examples 1 and 2 and Comparative Examples 1 and 2.

DETAILED DESCRIPTION OF THE INVENTION

The antiphlogistic analgesic adhesive of the present invention is used by applying the adhesive directly to the affected part through the pressure-sensitive adhesive layer.

It is to be understood that the above described disadvantages caused by application of an ointment are solved in utilization of the present invention.

The characteristics of the present invention are described below.

The flexible substrate used in the present invention is a substrate which prevents the pressure-sensitive adhesive layer from penetrating therethrough and functions to effectively prevent adhesion of the layer to clothing. Suitable flexible substrates include, for example, paper, woven and non-woven cloths prepared from cotton, rayon, polyamides, polyesters, etc., foamed sheets having a thickness of about 200 to about 5,000μ, preferably about 200 to about 1,000μ, prepared from polyethylene, urethane, rubber, polyvinyl chloride, etc., synthetic resin films having a thickness of about 10 to about 200μ prepared from polyethylene, polyester, polyamide, polyvinyl chloride, rubber, polyurethane, ethylene vinyl acetate, etc. synthetic resin. In materials having a low moisture permeability, it is preferred to provide the material with moisture permeability (preferably 5 to 2000 g/m²/24 hr.) using physicochemical processing, by which traces, such as those producing a rash, etc. caused by restricted air flow are prevented on the skin. Further, the above described substrate preferably has a property of expanding in at least one direction to prevent a disagreeable sense of tension. With a substrate which is not elastic, a suitable processing for providing elasticity is suitably carried out. When the substrate has elasticity, the substrate follows the expansion and contraction of the skin when applied to the body.

In the present invention, as an adhesive component in the pressure-sensitive adhesive material formed on the above described substrate, acrylic copolymers which have pressure-sensitive adhesive properties at room temperature (e.g., about 20° to about 30° C.) can be used.

Suitable acrylic copolymers which have pressure-sensitive adhesive properties at room temperature are composed of, as essential components, an alkyl acrylate having 4 to 12 carbon atoms in the alkyl moiety and a functional monomer having a functional group in the molecule and/or a vinyl monomer.

A suitable number average molecular weight for the above described copolymer is about 20,000 to about 500,000 preferably 30,000 to 300,000. This molecular weight range satisfies the requirement that an excellent adhesive property to the skin is obtained even if other additives are present with the copolymer and there is no residue remaining on the skin after stripping.

Examples of suitable alkyl acrylates include amyl acrylate, butyl acrylate, hexyl acrylate, heptyl acrylate, octyl acrylate, nonyl acrylate, 2-ethylhexyl acrylate, dodecyl acrylate, etc.

Suitable functional monomers having a functional group include those generally known having a functional group such as a carboxyl group, a hydroxyl group, an amino group, an amido group, an epoxy group, etc. However, the following two kinds of functional monomers are preferred from the standpoint of the adhesive property to the skin (particularly, when sweating) and a cohesive property.

One preferred functional monomer is functional monomer having a carboxyl group in the molecule, such as acrylic acid, methacrylic acid, itaconic acid, maleic acid, crotonic acid, etc.

The other preferred functional monomer is a functional monomer having a hydroxyl group in the molecule, such as hydroxymethyl acrylate, hydroxymethyl methacrylate, hydroxyethyl acrylate, hydroxyethyl methacrylate, hydroxpropyl acrylate, hydroxypropyl methacrylate, hydroxybutyl acrylate, hydroxybutyl methacrylate, hydroxyamyl acrylate, hydroxyamyl methacrylate, hydroxyhexyl acrylate, hydroxyhexyl methacrylate, etc.

These functional monomers having a functional group in the molecule are incorporated into the copolymer in an amount of about 0.1 to about 20% by weight, preferably 1 to 10% by weight.

Suitable vinyl monomers which can be used are vinyl acetate, acrylonitrile, vinyl ether, vinyl pyrrolidone, vinyl propionate, alkyl methacrylate having 1 to 10 carbon atoms in the alkyl moiety thereof, etc. However, use of vinyl acetate is preferred from the standpoint of a active ingredient releasing property, safety with respect to skin stimulation and improvement of adhesive properties to the skin, etc.

These vinyl monomers are incorporated into the copolymer in an amount of about 1 to about 50% by weight, preferably 20 to 45% by weight.

In producing acrylic copolymers having pressure-sensitive adhesive properties at room temperature from the above described composition, it is possible to use a suitable amount (e.g., about 0.05 to about 1 part by weight per 100 parts by weight of the monomer) of azo compounds such as azobisisobutyronitrile or peroxides such as benzoyl peroxide, as a polymerization initiator. For the polymerization, solution polymerization is preferred, but emulsion polymerization and bulk polymerization, etc. may be employed.

In the present invention, the amount of indomethacin incorporated in the above described pressure-sensitive adhesive layer is about 5 to about 100 mg per gram of the copolymer. However, the amount may be larger or smaller than the above described range depending on the symptoms of the affected part to be treated.

Indomethacin is generally homogeneously dissolved in the pressure-sensitive adhesive layer, but it may be dissolved, if desired, only in a surface layer contacting the skin where the pressure-sensitive adhesive layer is composed of a multilayer such as two layers.

If indomethacin is incorporated along in the above described copolymer, some degree of therapeutic effect is obtained just after application to the skin. It has been, however, found that the greater part of indomethacin present does not contribute to curing of the affected part because of crystallization of the indomethacin.

While not desiring to be found, the reason is believed to be that diffusion of indomethacin in the copolymer occurs less and the diffusion and permeation of indomethacin are prevented by the highly cross-linked matrix of protein fibrous materials in the keratin layer of the skin.

It has now been found that release of indomethacin from the copolymer and absorbability by the skin are remarkably improved by adding a liquid material having a specific property in a prescribed amount to the system comprising the above described copolymer and indomethacin.

This liquid material must function to keep the indomethacin in a solubilized state in the copolymer and the function of diffusing indomethacin into the skin. Therefore, because of this function this liquid material is described herein as "an absorption accelerating assistant" in this specification.

Since this absorption accelerating assistant is incorporated in the copolymer together with indomethacin, it must have a solubility parameter (generally referred to as a SP value) of 11 or less and preferably, 7.5 or more. A solubility parameter of more than 11 is not preferred, because compatibility with the copolymer is inferior causing the so-called deterioration of adhesive properties by the absorption accelerating assistant to occur.

As a result of further experiments, it has been found that the difference in the SP value between indomethacin and the absorption accelerating assistant should be 2 or less.

Namely, if the compatibility or indomethacin (SP value: 8.8) with the absorption accelerating assistant is insufficient, the solubility of indomethacin in the absorption accelerating assistant is inferior so that the effect of addition of the absorption accelerating assistant is not exhibited. On the other hand, if the compatibility of indomethacin with the absorption accelerating assistant is too good, release of indomethacin deteriorates, because indomethacin is retained by the absorption accelerating assistant.

Further, the absorption accelerating assistant used is selected so that the characteristics of the acrylic copolymer are substantially not damaged.

Suitable examples of liquid material which can be used as the absorption accelerating assistant satisfying the above requirements are aliphatic acid esters, for example, caproic acid esters such as ethyl caproate (SP value: 10.5), etc., adipic acid esters such as diisopropyl adipate (SP value: 9.2), dibutyl adipate (SP value: 9.2) or dibutyldiglycol adipate (SP value: 8.6), etc., and sebacic acid esters such as diisopropyl sebacate (SP value: 9.2) or diethyl sebacate (SP value: 9.2), etc. In addition, partial esters prepared by reacting a polyhydric alcohol such as sorbitan with an aliphatic acid, polyoxyethylene glycol polyhydric alcohol acyl esters prepared by reacting such further with ethylene oxide, for example polyoxyethylene sorbitan monooleate (SP value: 9.02) or polyoxyethylene sorbitan monolaurate (SP value: 8.75), etc., and polyhydric alcohols, etc.

At least one absorption accelerating assistant is employed in an amount of about 1 to 30 parts by weight, preferably 3 to 20 parts by weight, based on 100 parts by weight of the acrylic copolymer, to produce the pressure-sensitive adhesive material used in the present invention.

The antiphlogistic analgesic adhesive of the present invention, as described above, comprises a combination of a specific acrylic copolymer, the absorption accelerating assistant and indomethacin so that a large amount of indomethacin is absorbed through the skin. Accordingly, the antiphlogistic analysic adhesive of this invention exhibits an excellent effect in curing the affected part under the skin.

The present invention is illustrated more specifically by reference to the following examples. The present inventions however, is not to be construed as limited to the following examples. In the examples, all parts are by weight unless otherwise indicated.

EXAMPLE 1

A reactor equipped with a reflux condenser and a stirrer was charged with 98 parts of 2-ethylhexyl acrylate, 2 parts of acrylic acid, 0.2 parts of benzoyl peroxide and 150 parts of ethyl acetate, and polymerization was carried out at 60° C. for 8 hours under a nitrogen atmosphere. The resulting solution of the copolymer (number average molecular weight: 35,000) was diluted with ethyl acetate to a solid content of 20% after drying.

To the solution of the acrylic copolymer, 5 parts of indomethacin and 10 parts of diethyl sebacate, based on 100 parts of the solid content of the solution, were added. This mixture was applied to a releasing paper and dried to form a pressure-sensitive adhesive layer containing indomethacin and diethyl sebacate. Then, a polyethylene film (thickness: 0.08 mm), a surface of which has been subjected to a corona discharge treatment, was put on the above described adhesive layer to face the treated surface to the adhesive layer, and they were adhered by pressing to produce an antiphlogistic analgesic adhesive with a releasing paper. The adhesive layer of the resulting adhesive contained 200 μg of indomethacin per square centimeter.

EXAMPLE 2

A reactor equipped with a reflux condenser and a stirrer was charged with 60 parts of 2-ethylhexyl acrylate, 40 parts of vinyl acetate, 0.2 parts of azobisisobutyronitrile and 120 parts of ethyl acetate, and polymerization was carried out at 60° C. for 8 hours under nitrogen atmosphere. The resulting solution of the copolymer (number average molecular weight: 78,000) was diluted with ethyl acetate to a solid content of 20% after drying.

To the resulting solution of the acrylic copolymer, 5 parts of indomethacin and as an absorption accelerating assistant 10 parts of diethyl sebacate based on 100 parts of the solid content of the solution were added. This mixture was applied to a releasing paper and dried to form pressure-sensitive adhesive layer containing indomethacin and the above described absorption accelerating assistant. Then an antiphlogistic analgesic adhesive equipped with the releasing paper was produced using the same procedures as in Example 1. The adhesive layer of the resulting adhesive contained 200 μg of indomethacin per square centimeter.

EXAMPLE 3

A reactor equipped with a reflux condenser and a stirrer was charged with 80 parts of butyl acrylate, 18 parts of vinyl acetate, 2 parts of acrylic acid, 0.2 parts of benzoyl peroxide and 150 parts of ethyl acetate, and polymerization was carried out at 60° C. for 8 hours under a nitrogen atmosphere. The resulting solution of the copolymer (number average molecular weight: 110,000) was diluted with ethyl acetate to a solid content of 20% after drying.

To the resulting solution of the acrylic copolymer, 5 parts of indomethacin, 5 parts of diisopropyl adipate (absorption accelerating assistant) and 5 parts of polyoxyethylenesorbitan monooleate (absorption accelerating assistant) based on 100 parts of the solid content of the solution were added. The resulting mixture was applied to a releasing paper and dried to form a pressure-sensitive adhesive layer containing indomethacin and the above described two absorption accelerating assistants. Then, an antiphlogistic analgesic adhesive equipped with a releasing paper was produced using the same procedure as in Example 1. The adhesive layer of the resulting adhesive contained 200 μg of indomethacin per square centimeter in a manner similar to Example 1.

EXAMPLE 4

A reactor equipped with a reflux condenser and a stirrer was charged with 95 parts of 2-ethylhexyl acrylate, 2 parts of hydroxyethyl acrylate, 3 parts of methacrylic acid, 0.2 parts of azobisisobutyronitrile and 150 parts of ethyl acetate, and polymerization was carried out at 60° C. for 8 hours under a nitrogen atmosphere. The resulting solution of the copolymer (number average molecular weight: 56,000) was diluted with ethyl acetate to a solid content of 20% after drying.

To the resulting solution of the acrylic copolymer, 5 parts of indomethacin and 10 parts of diisopropyl sebacate based on 100 parts of the solid content of the solution were added. The resulting mixture was applied to a releasing paper and dried to form a pressure-sensitive adhesive layer containing indomethacin and diisopropyl sebacate. Then, an antiphlogistic analgesic adhesive equipped with a releasing paper was produced using the same procedure as in Example 1. The adhesive layer of the resulting adhesive contained 200 μg of indomethacin per square centimeter in a manner similar to Example 1.

COMPARATIVE EXAMPLE 1

An antiphlogistic analgesic adhesive equipped with a releasing paper was obtained using the same procedure as in Example 1, except that 10 parts of diethyl sebacate were not added.

COMPARATIVE EXAMPLE 2

To an adhesive solution of 70 parts of styreneisoprene-styrene block copolymer (stylene content 14 wt%), 100 parts of liquid paraffin, 130 parts of synthetic polyterpene resin and 100 parts of toluene, indomethacin was added in an amount corresponding to 5 parts based on 105 parts of the solid content after drying, and the resulting mixture was applied to a releasing paper and dried. Then, an antiphlogistic analgesic adhesive equipped with a releasing paper was obtained using the same procedure as in Example 1. The adhesive layer of the resulting adhesive contained 200 µg of indomethacin per square centimeter similarly to Example 1.

The characteristics of each adhesive in Examples 1-4 and Comparative Examples 1-2 were determined as follows.

(1) Absorption Value Test

The back of guinea pigs was sheared to remove the fur. After a lapse of 1 day, the above described adhesives in Example 1 and Comparative Example 1 were applied respectively in an area of a size of 4 cm² to the skin for 8 hours. Thereafter, the adhesives were stripped off and the amount of indomethacin left in the pressure-sensitive adhesive layer was measured, by which an indomethacin absorption value (%) was calculated by comparison with the initial indomethacin content. The results were 29.4±2.5% in Example 1 and 12.6+3.7% in Comparative Example 1.

(2) Test for Suppression Value to Carrageenin-induced Untradermal Edema

6 Wistar male rats of a weight of about 250 g were used as a group. The back of each rat was sheared to remove the fur. After a lapse of 15 hours, a sample strip and a control strip were applied to one left and one right positions on the back. The adhesives of Examples 1 to 4 and Comparative Examples 1 to 2 which were cut to a size of 4 cm² were used as the sample strip. The adhesives produced in the same manner as in Examples 1 to 4 and Comparative Examples 1 to 2 except that indomethacin or the absorption accelerating assistant was not added were used as the control strip, which were cut in a size of 4 cm².

After a lapse of 2 hours from the application, the test strips were removed by stripping, and 0.05 ml of a 0.5% carrageenin physiological saline solution was injected into the parts of which the strips were applied. After 4 hours, the rats were sacrificed. The part of the skin were the irritant injected was separated and an edema area was cut in a diameter of 12 mm. The weight of the cut skin was measured and the difference in weight between the area to which the sample strip was applied and the area to which the control strip was applied was calculated as edema weight. The supression value of carrageenin-induced intradermal edema was calculated according to the following formula.

$$\text{Suppression Value to Carrageenin-induced Intradermal Edema} = \frac{V_c - V_s}{V_c} \times 100 \, (\%)$$

wherein $V_c$ and $V_s$ represent each the mean weight of intradermal edema in the group of rats to which the sample strip was applied and that in the group of rats to which the control strip was applied.

The results of the test are shown in the following Table 1.

TABLE 1

| | Suppression Value to Carrageenin-induced Intradermal Edema (%) |
|---|---|
| Example 1 | 31.8 |
| Comparative Example 1 | 18.9 |
| Example 2 | 35.5 |
| Example 3 | 29.6 |
| Example 4 | 23.2 |
| Comparative Example 2 | 11.9 |

(3) Test for Release Property in Water

The adhesives of Examples 1 and 2 and comparative Examples 1 and 2 were cut to a size of 16 cm², respectively. They were immersed in water at 30° C., and the relationship between the immersion time and the release rate (%) for indomethacin was determined. The results are as shown in the FIGURE. In the drawing, curve 1 shows the result for Example 1, curve 2 shows the result for Example 2, curve 3 shows the result for Comparative Example 1, and curve 4 shows the result for Comparative Example 2.

EXAMPLE 5

Antiphlogistic analgesic adhesives were produced using the same procedures as in Example 1, except that diethyl sebacate was added in amounts of 5 parts and 15 parts per 100 parts of the copolymer. The adhesive strength and retentive force of the adhesives were determined.

The results obtained are shown in Table 2 below.

TABLE 2

| | Amount Added | | |
|---|---|---|---|
| | 5 parts | 10 parts* | 15 parts |
| Adhesive Strength (g/10mm width) | 525 | 407 | 336 |
| Retentive Force (minute) | 3.4 | 1.3 | 1.0 |

*Example 1

The methods of measurement in Table 2 were as follows.

Adhesive Strength:
A sample having a width of 10 mm was adhered to a Bakelite plate. The adhesive strength was then measured by stripping the sample by drawing the sample at an angle of 180° at a drawing rate of 300 mm/min. (condition: 23° C.×65% R.H.).

Retentive Force:
To an end of a Bakelite plate, an end of a sample having a width of 10 mm was adhered so that the adhered end was 20 mm in length. The other end of the sample was weighted with a 300 g weight, and the period of time at which the sample fell from the Bakelite plate was measured.

EXAMPLE 6

To a solution of a copolymer as described in Example 1, indomethacin was added in the amount shown in Table 3 below per square centimeter and 15 parts of dibutyl glycol adipate based on 100 parts of said solution were added as the absorption accelerating assistant to produce antiphlogistic analgesic adhesives. The results of application testing for 2 hours are shown in Table 3 below.

TABLE 3

| Amount Added ($\mu g/cm^2$) | Suppression Value to Carrageenin-induced Intradermal Edema (%) |
|---|---|
| 100 | 23.7 |
| 200 | 26.1 |
| 400 | 35.3 |
| 200* | 20.4 |

*80 mg of a gel containing 1 wt % of indomethacin was applied and covered with a cellophane adhesive sheet.

While the invention has been described in detail and with reference to specific embodiments thereof, it will be apparent to one skilled in the art that various changes and modifications can be made therein without departing from the spirit and scope thereof.

What is claimed is:

1. An antiphlogistic analgesic adhesive which comprises
   a flexible polymer substrate and
   an indomethacin containing pressure-sensitive adhesive layer closely contacting said flexible substrate, wherein said pressure-sensitive adhesive layer comprises a mixture of
   (a) indomethacin in an amount of about 5-100 mg per gram of a copolymer, where the copolymer is,
   (b) a copolymer of (i) an alkyl acrylate having 4 to 11 carbon atoms in the alkyl moiety and (ii) a functional monomer having a functional group in the molecule thereof and/or a vinyl monomer, which has pressure-sensitive adhesive properties at room temperature, said copolymer having an average molecular weight of about 20,000 to 500,000, and
   (c) an absorption accelerating assistant consisting of an aliphatic acid ester and polyoxyethylene glycol polyhydric alcohols, which has a solubility parameter (SP) of 11 or less and has skin diffusibility.

2. The antiphlogistic analgesic adhesive according to claim 1, wherein the alkyl acrylate is at least one alkyl acrylate selected from the group consisting of amyl acrylate, butyl acrylate, hexyl acrylate, heptyl acrylate, octyl acrylate, nonyl acrylate and 2-ethylhexyl acrylate.

3. The antiphlogistic analgesic adhesive according to claim 1, wherein the functional monomer is a monomer which has a carboxyl group.

4. The antiphlogistic analgesic adhesive according to claim 3, wherein the functional monomer having a carboxyl group is at least one monomer selected from the group consisting of acrylic acid, methacrylic acid, itaconic acid, maleic acid anhydride and crotonic acid.

5. The antiphlogistic analgesic adhesive according to claim 1, wherein the functional monomer is a monomer which has a hydroxyl group.

6. The antiphlogistic analgesic adhesive according to claim 5, wherein the functional monomer having a hydroxyl group is at least one monomer selected from the group consisting of hydroxymethyl acrylate, hydroxymethyl methacrylate, hydroxyethyl acrylate, hydroxyethyl methacrylate, hydroxypropyl acrylate, hydroxypropyl methacrylate, hydroxybutyl acrylate, hydroxybutyl methacrylate, hydroxyamyl acrylate, hydroxyamyl methacrylate, hydroxyhexyl acrylate and hydroxyhexyl methacrylate.

7. The antiphlogistic analgesic adhesive according to claim 1, wherein the vinyl monomer is vinyl acetate.

8. The antiphlogistic analgesic adhesive according to claim 1, wherein the amount of the functional monomer in the copolymer is about 0.1 to about 20% by weight.

9. The antiphlogistic analgesic adhesive according to claim 1, wherein the amount of the vinyl monomer in the copolymer is about 1 to about 50% by weight.

10. The antiphlogistic analgesic adhesive according to claim 1, wherein the difference in the solubility parameter between indomethacin and the absorption accelerating assistant is 2 or less.

11. The antiphlogistic analgesic adhesive according to claim 1, wherein the aliphatic acid ester is at least one aliphatic acid ester selected from the group consisting of adipic esters, sebacic acid esters and caproic acid esters.

12. The antiphlogistic analgesic adhesive according to claim 1, wherein the absorption accelerating assistant is polyoxyethylene glycol polyhydric alcohols.

13. The antiphlogistic analgesic adhesive according to any of claims 1, 8, or 12, wherein the weight ratio of the copolymer to the absorption accelerating assistant is about 1:0.01 to about 1:0.3.

* * * * *